United States Patent [19]

Hammond et al.

[11] Patent Number: 6,077,521

[45] Date of Patent: Jun. 20, 2000

[54] METHODS FOR MOSQUITO ABATEMENT

[75] Inventors: David G. Hammond, Berkeley; Isao Kubo, Moraga, both of Calif.

[73] Assignee: The Regents of the University of California, Oakland, Calif.

[21] Appl. No.: 09/057,103

[22] Filed: Apr. 7, 1998

[51] Int. Cl.[7] .......................... A01N 25/00; A01N 31/00; B01F 17/00
[52] U.S. Cl. .......................... 424/405; 252/351; 252/352; 514/724
[58] Field of Search .............................. 424/405; 252/351, 252/352; 514/724

[56] References Cited

U.S. PATENT DOCUMENTS

| 4,160,033 | 7/1979 | Garrett et al. | 514/473 |
| 4,569,947 | 2/1986 | Stockton et al. | 514/724 |

OTHER PUBLICATIONS

Keirans et al. Mosquito News (in J. Am. Mosq. Control Assoc.) vol 28, No. 1, pp. 71–74, 1968.

Sinniah, B. Trans. Royal Soc. Trop. Med. Hyg. vol. 77, No. 1, pp. 35–38, 1983.

Hammond et al. Bioorganic and Med. Chem. vol. 7, No. 2, pp. 271–278, abstract enclosed, 1999.

Sigma Chemical Catalog, p. 1645, 1994.

*Primary Examiner*—Leon B. Lankford, Jr.
*Assistant Examiner*—Christopher R. Tate
*Attorney, Agent, or Firm*—Richard Aron Osman

[57] ABSTRACT

Mosquito abatement is effected by administering to a water source containing mosquitoes an effective amount of a water-insoluble alcohol in a water-miscible form. The water-miscible form is provided in a wide variety of ways such as mechanical agitation (e.g. sonication), addition of a surfactant (e.g. a detergent), etc. The invention also provides labeled containers, including dispensers, containing a composition comprising a water-insoluble alcohol in a water miscible form and an affixed legible label providing instructions for the use of the composition for mosquito abatement.

21 Claims, 3 Drawing Sheets

FIG. 3

METHODS FOR MOSQUITO ABATEMENT

FIELD OF THE INVENTION

The field of this invention is mosquito abatement.

BACKGROUND

Despite significant advances in the techniques used for its control during recent decades, the mosquito continues to pose serious public health problems as we approach the 21$^{st}$ Century. In addition to the persistent irritation they cause humans and animals simply by virtue of their blood-sucking behavior and the itching this causes, mosquitoes are also the principal vector of a variety of serious diseases, including malaria, yellow fever, dengue, and encephalitis. Worldwide, approximately 2.7 million human deaths occur each year solely as a result of malaria transmitted by mosquitoes [1].

We disclose herein the use of alkanols applied to water as soluble solutions for the control of mosquitoes in their larval stage. Exemplified species include *Culex tarsalis*, the principal vector of the Western equine and St. Louis encephalitis viruses common throughout the Western U.S., and *Culiseta incidens*. To understand the molecular basis of alkanol toxicity, a variety of unsaturated long-chain alcohols were also tested, including, farnesol which may act in some insects as a juvenile hormone mimic [2].

Primary alkanols are important flavor and fragrance compounds that are found throughout the plant kingdom, occur naturally in everyday foods and beverages [3], and are widely used as food additives [4]. Homologues containing 12 or more carbons are only sparingly soluble in water and their tendency to form monomolecular layers over the surface of a body of water was examined decades ago as a means to reduce evaporative losses [5]. Because monolayers lower surface tension, it was also suggested that they might be used in pest control to suffocate the aquatic stages of mosquitoes or prevent recently emerged adults from launching off the water's surface. Consequently, all earlier research employing alkanols against mosquitoes has attributed lethality entirely to reduced surface tension, wetting of their hydrofuge structures, or other surface-related phenomena [6–10]. However, here we disclose that there is a more immediate and lethal effect of 1-alkanols on mosquito larvae, that it is unrelated to surface tension, and is biochemical rather than physical.

A review of the literature indicates that this is the first comprehensive study of the structure-activity relationship for the full series of alkanols against mosquitoes. Primary alkanols are also known to act as general anesthetics [11,12], and increasing potency has been correlated to increasing chain length [13] until a point of cutoff is reached, usually at 1-dodecanol, after which activity disappears entirely [14,15]. In mosquitoes, we found that activity levels off after undecanol ($C_{11}$) but does not disappear until after pentadecanol ($C_{15}$). Mosquitoes appear to be the first animal for which cutoff has been demonstrated to occur at a chain length beyond $C_{12}$, offering new insights into the molecular basis of anesthetic cutoff and demonstrating that alkanols may be used for selective pest control.

Cited Literature

1. D. Butler, Nature 386 (1997) 535–536.
2. P. Schmialek, Z. Naturforschg. 16b (1961) 461–464.
3. Flavor and Extract Manufacturers' Ass'n of the U.S. (December, 1975), U.S. Dept Commerce, NTIS #PB254-974.
4. G. A. Burdock (1995) Fenaroli's Handbook of Flavor Ingredients, 3$^{rd}$ed, CRC Press, Cleveland, Ohio.
5. W. J. Wiltzius (1967), U.S. Dept. of the Interior, Bureau of Reclamation; Water Resources Technical Publication, Research report no. 7.
6. G. A. Lorenzen, W. W., Mosquito News 28 (1968) 230–232.
7. M. A. Badalmente, et al., Ann. Entomol. Soc. Am. 69 (1976) 114–116.
8. B. Sinniah, T. Roy. Soc. Trop. Med. H. 77 (1983) 35–38.
9. A. I. McMullen, M. N. Hill, Nature 234 (1971) 51–52.
10. A. I. McMullen, P. Reiter, M. C. Phillips, Nature 267 (1977) 244–245.
11. H. Meyer, Arch. Exp. Path. Pharmakol. 42 (1899) 109–118.
12. E. Overton, Studien Über Die Narkose (1901) Fischer, Jena, G. D. R.
13. K. H. Meyer, H. Hemmi, Biochem. Z. 277 (1935) 39–71.
14. J. Alifimoff, L. L. Firestone, K. W. Miller, Brit. J. Pharmacol. 96 (1989) 9–16.
15. G. D. Veith, D. J. Call, L. T. Brooke, Can. J. Fish. Aquat. Sci. 40 (1983) 743–748.
16. World Health Organization, (1963), in Insecticide resistance and vector control: thirteenth 1. report of the WHO Expert Committee on Insecticides. Technical report series; 265, pp. 51–55, WHO, Geneva.
17. P. F. Russell, T. R. Rao, Amer. J. Trop. Med. 21 (1941) 767–777.
18. P. Reiter, Mosquito News 38 (1978) 334–337.
19. R. Levy, J. J. Chizzonite, W. D. Garrett, T. W. Miller, Mosquito News 42 (1982) 1–11.
20. M. S. Mulla, H. A. Darwazeh, L. L. Luna, Mosquito News 43 (1983) 489–495.
21. M. J. Pringle, K. B. Brown, K. W. Miller, Mol. Pharmacol. 19 (1981) 49–55.
22. K. W. Miller, et al., Proc. Natl. Acad. Sci. USA 86, (1989) 1084–1087.
23. J. S. Chiou, S. M. Ma, H. Kamaya, I. Ueda, Science 248 (1990) 583–585.
24. T. W. Schultz, et al., Ecotox. Environ. Safe. 19 (1990) 243–253.
25. I. Kubo, H. Muroi, A. Kubo, Bioorgan. Med. Chem. 3 (1995) 873–880.
26. M. Hattori, et al. Chem. Pharm. Bull. 35 (1987) 3507–3510.
27. N. P. Franks, W. R. Lieb, Nature 367 (1994) 607–614.
28. N. Rodriguez, R. Villegas, J. Requena, J. Membrane Biol. 104 (1988) 139–146.
29. J. R. Elliot, A. A. Elliot, Progress in Neurobiology 42 (1994) 611–683.
30. S. N. Treistman, A. Wilson, Proc. Nat. Acad. Sci. USA 84 (1987) 9299–9303.
31. K. G. Mongo, G. Vassort, J. Mol. Cell. Cardiol. 22 (1990) 939–954.
32. R. D. Murrell, M. S. Braun, D. A. Haydon, J. Physiol-London 437 (1991) 431–448.
33. N. P. Franks, W. R. Lieb, Nature 316 (1985) 349–351.
34. N. P. Franks, W. R. Lieb, Proc. Nat. Acad. Sci. USA 83 (1986) 5116–5120.
35. M. H. Abraham, W. R. Lieb, N. P. Franks, J. Pharm. Sci. 80 (1991) 719–724.
36. G. W. J. Moss, W. R. Lieb, N. P. Franks, Biophys. J. 60 (1991) 1309–1314.
37. R. D. Swisher (1970) Biodegradation Data, in Surfactant Biodegradation (R. D. Swisher, ed.), Marcel Dekker, New York, N.Y.
38. D. L. J. Opdyke, Food and Cosmetics Toxicology 11 (1973) 1011–1082.
39. C. N. Huhtanen, J. Food Protect. 43 1980 195–196.

SUMMARY OF THE INVENTION

The invention provides methods and compositions for mosquito abatement. In general, the methods involve administering to a water source containing mosquitos an effective amount of a water-insoluble alcohol in a water-miscible form. The water-miscible form may be provided in a wide variety of ways such as mechanical agitation (e.g. sonication), addition of a surfactant (e.g. a detergent), etc. Preferred alcohols are primary, secondary or tertiary, nonaromatic, unsubstituted, saturated or unsaturated, branched or unbranched, and have an overall chain length of 8 to 16 carbons. In a particular embodiment, the alcohol is nonaromatic, unsubstituted, unbranched and has 8–15 carbon atoms, and in a more particular embodiment, the alcohol is tri, tetra or pentadecanol. The invention also provides labeled containers, including dispensers, containing a composition comprising a water-insoluble alcohol in a water miscible form and an affixed legible label providing instructions for the use of the composition for mosquito abatement.

BRIEF DESCRIPTION OF THE FIGURES

FIG. 3. Comparison of biological activity of 1-alkanols against various organisms.

DETAILED DESCRIPTION OF PREFERRED EMBODIMENTS OF THE INVENTION

Figure 1:
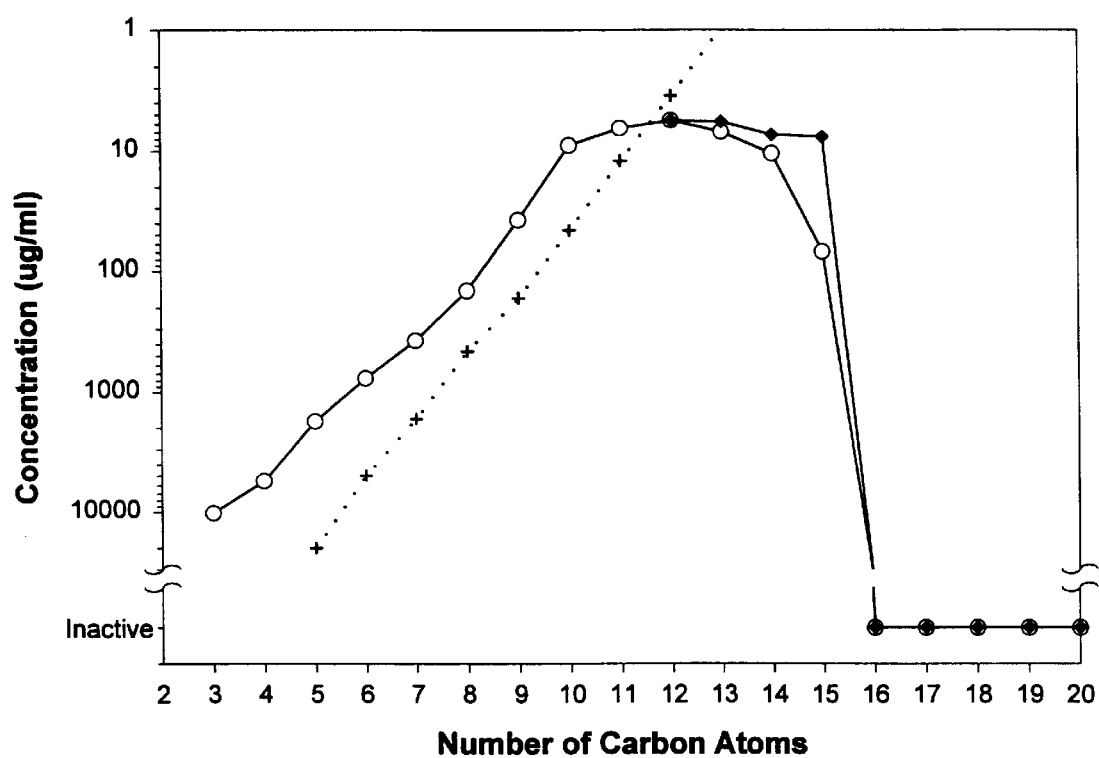
FIG. 1. 24 hr $LC_{50}$ concentration of 1-alkanols against $1^{st}$ instar *Culex tarsalis* larvae.

The following preferred embodiments and examples are offered by way of illustration and not by way of limitation.

The invention provides water-insoluble alcohol-based methods and compositions for mosquito abatement. The methods involve administering to the subject water source an effective amount of a water-insoluble alcohol in a water-miscible form, which form may be provided by any of a wide variety of means which enhance water-miscibility of the alcohol(s) used. For example, the administered composition, a fraction thereof, or the treated water source may be subjected to mechanical agitation in the form of sonication, vortexing, induced turbulence, mixing, shaking, stirring, etc. In a particular embodiment, the administered composition comprises a supersaturated solution of the subject alcohol.

In addition, a wide variety of additives, such as solvents, including acetone, ether, shorter chain alcohols like ethanol, etc., surfactants, including detergents, soaps, etc., etc., may be used in the compositions to enhance water-miscibility. Optionally, the compositions may also conveniently include other agents, such as agents which enhance stability, reduce degredation, retard evaporation, maintain suspension, provide color or odor markings, etc.

The enhancement is sufficient to increase the water miscibility of the subject alcohol(s) over diffusion from a surface application, preferably increasing the effective volumetric concentration by at least 2-fold, more preferably by at least one, two, three, four or five orders of magnitude.

A wide variety of water immiscible alcohols are effective in the subject methods and compositions. Effective alcohols (i.e. toxic to mosquito larvae) are readily determined empirically, as described and exemplified below. Preferred alcohols demonstrate $LD_{50}$ toxicity at at less than 100 µg/ml, preferably less than 30 µg/ml, preferably less than 10 µg/ml, more preferably less than 3 µg/ml at 24 hr exposure, under laboratory, and preferably field conditions. In a particular embodiment, the alcohol is primary, secondary or tertiary, non-aromatic, unsubstituted, saturated or unsaturated, branched or unbranched, has an overall chain length of 8 to 16 carbons and is without other functional groups (other than hydroxyl groups) such as carboxyls, carbonyls, etc.; in a more particular embodiment, the alcohol is unbranched, non-cyclic and has 8–15 carbon atoms; and in yet a more particular embodiment, the alcohol is a primary alcohol, most particularly, tri, tetra or pentadecanol.

The compositions frequently provide a mixture of a plurality of active alcohols, which mixtures can act synergistically and/or conjunctively, e.g. tetradecanol and undecanol, which are found to be especially active against late and early stage instar larvae, respectively.

The invention provides labeled containers, such as 55-gallon drums, containing the subject water-immiscible alcohol(s) and an affixed legible label providing instructions for the use of the composition for mosquito abatement. For example, the label may provide instructions for enhancing or maintaining enhanced water-miscibility of the alcohol(s).

EXAMPLES

Mosquitoes. Eggs of *Culex tarsalis* (Breckenridge strain) were generously supplied by Laura Kramer of UC Berkeley's School of Public Health and by Steve Schutz of the Contra Costa Mosquito and Vector Control District. Larvae were maintained at room temperature (20° C.±2° C.) and fed on a slurry of TetraMin® flake food for tropical fish.

Chemicals. All alcohols were purchased from Aldrich Chemical Co., with the exception of linoleyl alcohol (cis, cis-9,12,-octadecadienol) and linolenyl alcohol (9,12,15-octadecatrienol), which were both purchased from Sigma (St. Louis, Mo.), and 1-octanol, from Takasago, Inc. All chemicals were of at least 97–99% purity (with the exception of farnesol and cis-11-hexadecenol, which were at least 95% pure) and were used without further purification. Tween-80® was purchased from ICI (Wilmington, Del.). Golden Bear Oil (GB-1111®), was obtained from the Alameda County Mosquito and Vector Control District, CA.

Bioassays. Bioassays were conducted at room temperature (20° C.±2° C.) using deionized water (20 ml) in 1 oz. clear plastic containers made by Plastics Inc. (St. Paul, Minn.). Alcohols were applied by solubilizing them first in acetone, then diluting in water to the appropriate concentration and briefly shaking to ensure mixing. Ten larvae were then pipetted into each 20 ml volume and observed for a minimum of 24 hours, when mortality was recorded. Controls were treated with the maximum amount of acetone applied to each alcohol assay, usually 0.1 ml. Acetone itself was found to have no effect on the larvae up to a concentration of 10,000 µg/ml.

All compounds were assayed against $1^{st}$ instar larvae and 1-octanol through 1-hexadecanol were also tested against $3^{rd}$ instar larvae. Assays were repeated at least 5 times. Compounds were tested at a minimum of five concentrations following range finding tests.

Due to their excessive clumping and general insolubility in water, alkanols with 15 or more carbons were tested only up to 160 µg/ml. For alkanols greater than 10 carbons, bioassays were repeated with the addition of the commercial surfactant Tween-80 (100 µg/ml) to see if improved solubility might increase activity. For assays employing surfactant, shaking was impractical, so solutions were added while sonicating the test water, which helped to maximize solubility and mixing.

Larvae were considered dead or moribund if they stopped moving for a prolonged period, were unable to resurface after sinking to the bottom of the container, and were still unable to respond after gentle probing with a small spatula, as described in [16]. Mortality among controls was zero for more than 95% of the assays, and in no instance did it exceed 10%.

In assays where larvae were trapped without air and prevented from any contact with the surface, each test solution was prepared as described above, then used to fill a 250 ml glass jar above its brim so as to form a meniscus; a petri dish was then slid horizontally across the mouth of the jar so that no air bubbles remained. The edge was sealed with petroleum jelly to prevent drying and leakage. Time required to manifest toxicity is expressed as the time at which the last bodily movement could be detected from the last survivor among 10 larvae, and values cited are the average of at least 3 experiments.

Surface tension experiments. Surface tension measurements were taken at 20° C. with a CSC-DuNouy Precision Tensiometer (#70535) from CSC Scientific, Inc. (Fairfax, Va.). This instrument employs the upward pulling ring (6 cm iridium-platinum ring) method of measurement, is then corrected for gravity, and is accurate to about±0.2 dynes/cm. Solutions were prepared by adding pure alkanols to 100 ml water, which was then shaken vigorously and allowed to rest until any bubbles present had subsided before measurements were taken. The ring was cleaned by flaming and the alkanol solution was mixed using a magnetic stirbar between each measurement. Values cited are the means of at least three consecutive measurements which were all within 0.5 dyne of one another.

Data Analysis. The $LC_{50}$ values reported are the means of an $LC_{50}$ calculated individually for at least 5 separate experiments, using nonlinear regression (SigmaPlot®), by fitting data to the 4 parameter sigmoidal logistic equation: $y=y^{\circ}+[a/(1+(x/x^{\circ})^{b})]$, (1), where a=maximum mortality, x=concentration, $x^{\circ}$=concentration at 50% amplitude, $y^{\circ}$=minimum mortality, and b=the difference between the concentrations at 25% and 75% amplitude.

Toxicity to mosquito larvae: Alkanols. The toxicity of the homologous series of primary alkanols against *Culex tarsalis* larvae was recorded as mortality after 24 hours and the results (Table 1) show that larvicidal activity peaks at 1-dodecanol, with an $LC_{50}$ of 5.58 µg/ml against $1^{st}$ instar and 5.25 µg/ml against mixed 3rd & 4th instar larvae.

TABLE 1

$LC_{50}$ values of 1-alkanols against *Culex tarsalis* larvae and surface tension, γ, at relevant concentration. Surface tension is given only up to undecanol because the longer species readily adsorb to the container walls and at high surface pressures a very small change in concentration can cause a large change in γ.

| 1-Alkanol | $1^{st}$ instar $LC_{50}$, µg,ml | $3^{rd}$ & $4^{th}$ instar $LC_{50}$, µg/ml | $\gamma^a$ at $LC_{50}$ (dynes/cm) |
| --- | --- | --- | --- |
| Methanol | >20,000 | | |
| Ethanol | >20,000 | | |
| Propanol | 10,233 (± 1,667) | | 58.8 |
| Butanol | 5,521 (± 271) | | 58.8 |
| Pentanol | 1,757 (± 361) | | 59.1 |
| Hexanol | 770 (± 120) | | 54.7 |
| Heptanol | 306 (± 37.3) | | 52.5. |
| Octanol | 145 (± 10.5) | 132 (± 18.1) | 47.1 |
| Nonanol | 37.5 (± 8.78) | 40.1 (± 3.68) | 50.0 |
| Decanol | 8.99 (± 2.36) | 12.8 (± 1.03) | 57.5 |
| Undecanol | 6.50 (± 0.89) | 7.85 (± 0.66) | 29.7 |

TABLE 1-continued $LC_{50}$ values of 1-alkanols against *Culex tarsalis* larvae and surface tension, γ, at relevant concentration. Surface tension is given only up to undecanol because the longer species readily adsorb to the container walls and at high surface pressures a very small change in concentration can cause a large change in γ.

| 1-Alkanol | $1^{st}$ instar $LC_{50}$, µg,ml | $3^{rd}$ & $4^{th}$ instar $LC_{50}$, µg/ml | $\gamma^a$ at $LC_{50}$ (dynes/cm) |
| --- | --- | --- | --- |
| Dodecanol | 5.58 (± 0.73) | 5.25 (± 0.40) | |
| Tridecanol | 6.72 (± 0.66) | 8.36 (± 1.14) | |
| Tetradecanol | 10.5 (± 2.15) | 8.45 (± 1.02) | |
| Pentadecanol | 68.9 (± 13.3) | 20.1 (± 6.34) | |
| Hexadecanol | >160 | 53.8 (± 11.4) | |
| Heptadecanol thru Eicosanol | >160 | | |
| Tridecanol + Tween | 5.72 (± 0.61) | | |
| Tetradecanol + Tween | 7.34 (± 1.03) | | |
| Pentadecanol + Tween | 7.66 (± 1.52) | | |
| Hexadecanol + Tween | >160 | | |
| Heptadecanol thru Eicosanol + Tween | >160 | | |
| Other Alcohols[b] | | | |
| cis-11-Hexadecen-1-ol | 7.74 (± 0.58) | | |
| Farnesol | 7.93 (± 0.83) | | |
| Linoleyl alcohol | 8.97 (± 1.26) | | |
| Linolenyl alcohol | 8.27 (± 0.46) | | |
| 1,10-Decanediol | >800 | | |
| cardol 15:3 | active | | |
| anacardic acid | active | | |
| cardanol 15:0 | active | | |
| geraniol | active | | |
| nerolidol | active | | |
| eugenol | active | | |
| cinnamyl alcohol | active | | |
| α-terpineol | active | | |
| 8 benzyl octanol | active | | |
| cyclodecane ethanol | active | | |

[a]Surface tension at 20° C.
[b]In combination with Tween-80 at 100 µg/ml

Activity increases through the series as chain length is lengthened to dodecanol, tapers off slightly from dodecanol to pentadecanol, and then cuts off at hexadecanol. No mortality at all resulted from treatments of methanol or ethanol up to 20,000 µg/ml. Alkanols with greater than 16 carbons were ineffective as mosquito larvicides because they did not consistently prevent larvae from surfacing and did not produce 50% mortality up to the maximum practical dosage, even when assays were extended to 4 days.

Addition of Tween to improve solubility increased the toxicity of tridecanol and tetradecanol slightly, and of pentadecanol by nearly a full order of magnitude (Table 1). Activity of primary alkanols with less than 13 or more than 15 carbons was unaffected by the use of surfactant or sonication. Tween itself had no noticeable toxicity to larvae up to 400 µg/ml, four times the concentration used here.

Sublethal doses provoked symptoms of anesthesia in mosquitoes, e.g., unresponsiveness to outside stimuli such as tapping on the container, and cessation of characteristic diving and feeding behaviors.

Whereas there was no appreciable difference between the patterns of physiological toxicity of alkanols to larvae of different instars, the lethal effects of reduced surface tension were most evident against $3^{rd}$ and $4^{th}$ instar larvae, which were less able than $1^{st}$ instars to tolerate prolonged periods without air—note the potency of pentadecanol and hexadecanol against late instars as compared to $1_{st}$ instar. In short, the effectiveness of hexadecanol against late instars only is apparently the result of its physical properties for temporarily lowering surface tension, and not of inherent biochemical toxicity (see Results of suffocation experiments).

Statistical analysis of the data showed that the difference in potency of 1-alkanols differing in length by one carbon was significant (p<0.01) for $C_3$–$C_{10}$ and for $C_{14}$–$C_{16}$. The difference between pentadecanol alone and pentadecanol+Tween was also significant (p<0.01). However, the differences among the most potent homologues ($C_{10}$–$C_{14}$) and the effects of combining each of these with Tween, were not significant for this dataset (n=5).

Other alcohols. In order to better understand the significance of the cutoff in activity after pentadecanol, several other alcohols of relevant structure and chain length were tested as well, all in combination with Tween to ensure maximum solubility. It was interesting to note that whereas hexadecanol was not toxic to $1^{st}$ instar mosquitoes at the highest concentrations tested, cis-11-hexadecenol was nearly as potent as the strongest of the saturated alkanols. Similarly, the introduction of two (in the case of linoleyl alcohol) or three (linolenyl alcohol) double bonds to octadecanol converted the compound from completely inactive to being among the most potent (Table 1).

The branched and unsaturated sesquiterpene farnesol, which has an overall length of 12 carbons, also showed toxicity comparable to that of dodecanol, leading us to infer that the toxicity depends on a particular balance between the hydrophobic and hydrophilic moieties. The head-tail type structure is apparently essential for larvicidal activity because whereas 1-decanol was toxic to mosquitoes in the range of 10 µg/ml, 1,10-decanediol was not toxic even at 800 µg/ml.

Although the differences in relative toxicity were consistent among the four unsaturated alkenols tested, they were not statistically significant (p<0.01 and n=5).

Surface tension experiments. The objective of the surface tension experiments was to test the hypothesis that the lethal concentration of a given alkanol can be positively correlated to the concentration required to lower surface tension enough to prevent larvae from surfacing for air. Dilute solutions of Ivory soap produce low, yet stable surface tension values, and were used to confirm the results of earlier researchers that some mosquito larvae have difficulty surfacing for air when surface tension (γ)—normally about 72 dynes/cm—is decreased to 27–36 dynes/cm [17]. For *C. tarsalis* we found variability among individuals, but most first and second instar larvae were unable to attach to the surface when γ was decreased to the range of 28 to 32 dynes/cm; fourth instar larvae were able to tolerate lower surface tensions, but none were able to tolerate γ below about 26 dynes/cm.

In contrast, the concentration of $C_3$–$C_{10}$ alkanol that caused 50% mortality in $1^{st}$ instar larvae produced surface tensions of 62 to 47 dynes/cm (Table 1), which allowed even the smallest larvae to surface without difficulty. The concentration of each $C_3$–$C_{10}$ alkanol necessary to lower γ to 30 dynes/cm was on average 8 times higher than its respective $LC_{50}$ concentration (FIG. 1). FIG. 1 illustrates that up to about decanol, the alkanol concentration needed to prevent larvae from surfacing is approximately 8 times the $LC_{50}$ concentration (○, Alkanols alone; ♦, Alkanols in combination with Tween-80; +, Dose required to lower surface tension to 30 dynes/cm). Surface tension data for $C_{10}$ through $C_{13}$ are estimates based on the pattern of experimental data for $C_3$ through $C_9$, whereby 30 dynes/cm was reached at approximately 85% of each alkanol's aqueous solubility. Furthermore, for chain lengths up to 10 carbons, many of the dead larvae were found with their respiratory siphons still firmly suspended from the water's surface, unequivocally eliminating surface phenomena as the cause of death.

Alkanols with 11–16 carbons, on the other hand, were found to be superior surface tension reducing agents and even at low doses, larvae attempting to surface for air simply bounce off the air-water interface and sink back downward. Nevertheless, the swiftness of death hinted that even these larvae were succumbing to a biochemical phenomenon long before they could be expected to display the effects of suffocation. For these long-chain alkanols, the importance of a biochemical mode of action was demonstrated by using a method that prevented contact with the surface for the course of the assay (see following section).

Suffocation experiments. Mosquito larvae, especially early instars, can survive for extended periods without access to air, apparently by cutaneous respiration of dissolved oxygen in the water [18]. A glass ceiling such as a petri dish can be used to trap larvae without air. By creating a test system free of air and its associated interfaces, the container ceiling is effectively made identical to its walls and bottom and, most importantly, the larvae are specifically isolated from any surface-related phenomenon that might wet their siphon opening, reduce its hydrofuge properties, or allow leaks into their respiratory siphons during attempts to surface.

When we trapped twenty $1^{st}$ instar *C. tarsalis* larvae under glass without air as a control, 100% were alive and active 16 hours later. ($4^{th}$ instar populations survived only about 3–4 hours.) Survival time of $1_{st}$ instar larvae under glass was approximately doubled to 32–48 hrs by lowering the temperature of the water to 8–10° C.

Figure 2:
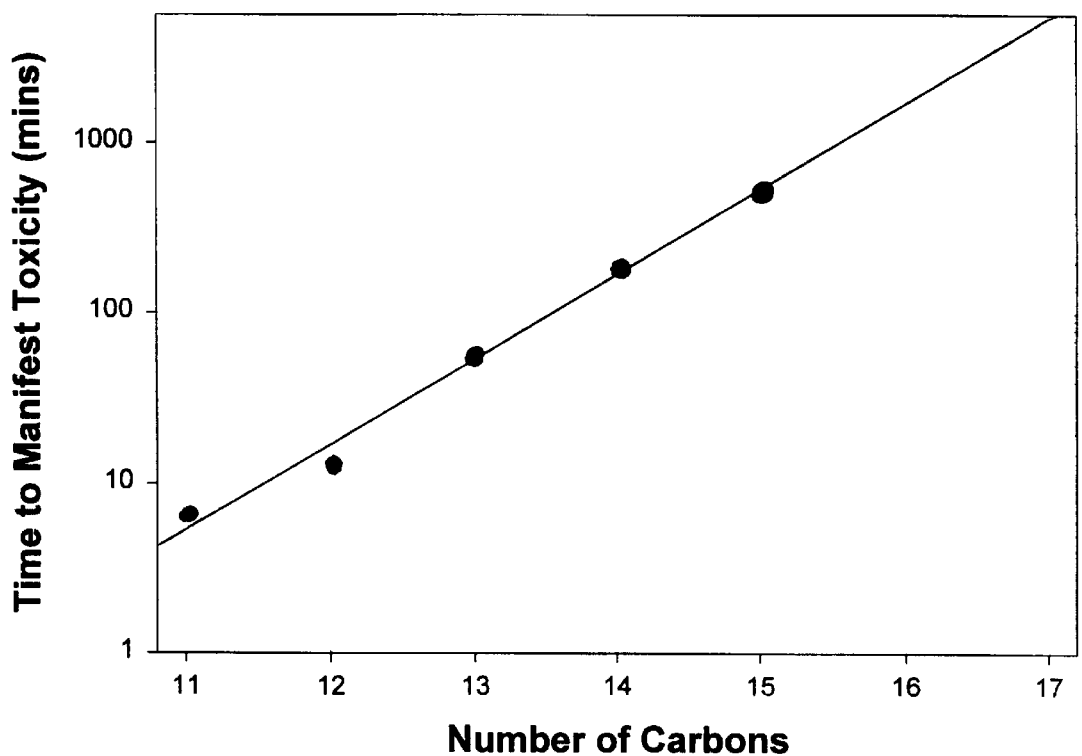
FIG. 2. Time dependency of 1-alkanol toxicity in mosquito larvae.

In contrast, $1^{st}$ instar larvae trapped without air in jars of water treated with decanol or undecanol were immobilized on the bottom and made no further efforts to surface after just 5 minutes; the same result was observed with dodecanol after about 12 minutes, with tridecanol after an hour, with tetradecanol after 3 hours, and with pentadecanol after approximately 9 hours. Extrapolation of this time dependency curve (FIG. 2) predicts activity for hexadecanol after about 18 hours, but no mortality due to hexadecanol nor heptadecanol treatments occurred before control larvae themselves began to die of anoxia, after about 24–30 hrs (in the figure, each point represents the mean time after treatment when the last bodily movement was observed from any of 10 treated larvae when trapped without air under glass. Error bars show the range for 3 experiments. Alkanols of $C_{10}$ through $C_{14}$ at 20 µg/ml, $C_{15}$ through $C_{17}$ at 60 µg/ml; no mortality for $C_{16}$ or $C_{17}$ before controls themselves began to die, at 24–30 hrs. All solutions prepared with Tween and sonication). Nevertheless, we still considered the possibility that hexadecanol may act by a mechanism similar to but weaker than shorter chain homologues, for example as a partial anesthetic.

In an effort to extend the survival of larvae trapped without air and thereby allow sufficient time for the possibility that hexadecanol might still show activity at longer exposures, the same air-free experiments were also carried out under refrigeration, at 6, 10, and 14° C. Control larvae were thus able to survive about 48 hours, but we were surprised to find that 60 µg/ml pentadecanol+Tween, which had caused 100% mortality at 20° C., caused just 20% mortality at 14° C., and toxicity disappeared entirely at 10° C. or less. Comparatively, the toxicity and time dependency of tetradecanol and the shorter chain alkanols were unaffected by these lower temperatures, indicating that the loss of activity is at least partially a function of declining solubility.

Reversibility. Subsequent experiments, in which larvae treated with lethal doses of $C_{10}$–$C_{15}$ alkanols were transferred to clean water well after the on-set of anesthesia had become evident, confirmed that the effects were completely reversible. Within minutes or hours, again dependent on chain length, larvae returned to behavior indistinguishable from that of untreated larvae.

Discussion. Our findings challenge the previously accepted belief that alkanols act as mosquitocides only via suffocation provoked by surface phenomena; and, for studies measuring biological activity of the alkanol series, provide the first demonstration of cutoff occurring in an animal at a chain length beyond $C_{12}$.

The speed with which alkanols $\leq C_{15}$ act as mosquito larvicides is in sharp contrast to the conclusions of previous researchers using insoluble monolayers of dodecanol [6,9], hexadecanol [9], and lecithins [10], which were specifically described as producing larval death only after the dissolved oxygen content of the water was depleted, usually overnight. The increasingly time-dependent nature of toxicity as chain length is increased offers further evidence of the biochemical mode of action for alkanols, independent of any suffocation mechanism resulting from reduced surface tension at the air-water interface. Action of farnesol was also rapid, so although it may act as a juvenile hormone mimic in some insects, hormonal disturbances take time, and our data indicate that its toxicity against mosquito larvae is via the same mechanism as unbranched, saturated alcohols.

When, for comparison purposes, we treated mosquitoes with Golden Bear Oil, a commercial product sold as a surface-active mosquitocide, $4^{th}$ instar larvae died after a period of several hours-consistent with an explanation of death via suffocation—and $1^{st}$ instar larvae were weakened, but still alive, 24 hours later. Alkanols, in contrast, were generally observed to act more quickly on $1^{st}$ instar than on $4^{th}$ instar larvae. Also, whereas pupae have been shown previously to be more susceptible to monolayers than larvae [19,20,9], our findings indicate that solutions of long chain alkanols are more toxic to Culex larvae than to the pupae, possibly owing to the pupae's thicker cuticle and concomitant capacity to resist penetration by foreign substances.

Tests with animals in vivo are somewhat limited, but long chain alkanols are known to produce anesthesia in fathead minnows [15], tadpoles [21,22,14], and brine shrimp [23], and to cause growth impairment in the ciliate protozoan *Tetrahymena pyriformis* [24]. In our own earlier studies, they showed activity against a variety of gram-positive bacteria and fungi, but not against gram-negative bacteria [25].

Figure 3:
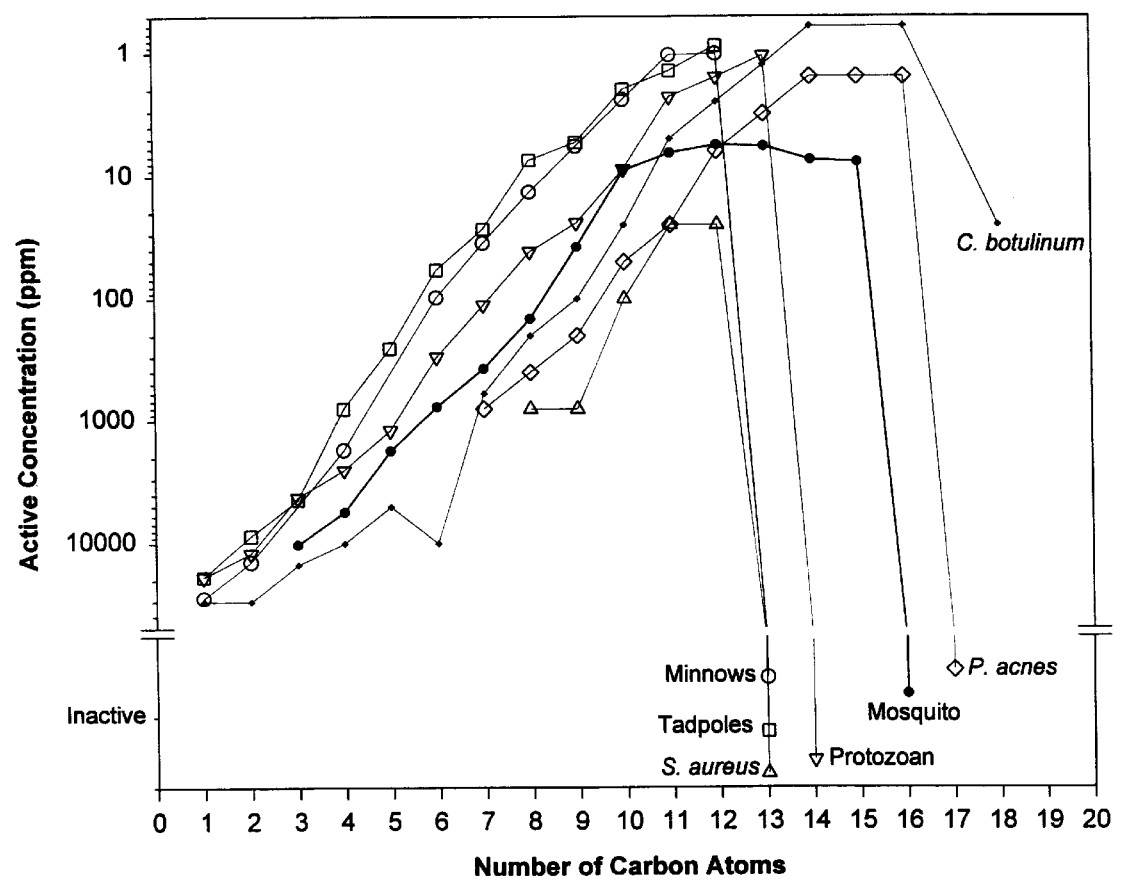

A persistent quandary facing researchers has been the "cutoff" phenomenon, whereby potency increases with chain length until reaching a maximum, and the alkanol containing a single additional carbon shows no potency at all, even when duration of exposure lasts several days [22]. Although attention has focused on instances where cutoff occurs immediately after dodecanol, the exact length of carbon chain where cutoff occurs clearly varies among genera (FIG. 3), and even among strains of the same species in the case of bacteria (data on *Streptococcus mutans* from [25] and [26]). FIG. 3 shows that the cutoff in activity against fish and tadpoles occurs after $C_{12}$, but in mosquitoes not until after $C_{15}$. Although the endpoints measured are not identical in all test systems, sublethal doses provoked symptoms of anesthesia in mosquitoes and growth inhibition in microorganisms. The legend for the figure is as follows: □ Tadpole (*Rana pipiens*), loss of righting reflex, $EC_{50}$[14]; ○ Minnow (*Pimephales promelas*), 96 hr $LC_{50}$[15]; ▽ Protozoan (*Tetrahymena pyriformis*), inhibitory growth concentration, $EC_{50}$[24]; △ *S. aureus*, minimum bactericidal concentration, $EC_{50}$[25]; ● Mosquito (*Culex tarsalis*), 24 hr $LC_{50}$; Tween used to maximize solubility of alkanols $\geq C_{13}$; ◇ *Propionibacteruim acnes*, minimum bactericidal concentration, $EC_{50}$[25]; +*Clostridium botulinum*, minimum inhibitory concentration [39].

Our review of the literature found no other animal for which cutoff had been reported at a chain length beyond dodecanol, which may be the result of differences in the membrane composition of test organisms. By comparison, tadpoles were fully anaesthetized by nonanol after 30 min, by decanol and undecanol after 60 min, by dodecanol after 120 min, but not by tridecanol, even when exposed for 96 hours [14]. Mosquitoes are also unusual in that the loss of activity is gradual, tapering off from the strongest compounds before disappearing, whereas for most organisms, maximum activity occurs at a given chain length of n, and absolutely no activity is present at the alkanol of chain length n+1. For example, the minimum bactericidal concentration against *Propionibacterium acnes* was just 1.56 $\mu$g/ml for hexadecanol, but heptadecanol was completely inactive, even when tested at 800 $\mu$g/ml [25].

The precise anaesthetic mechanism is still not well understood, and attempts to explain it have covered a wide array of biological functions, mostly related to structure and function of lipid membranes and/or proteins [27]. The increase in activity with chain lengthening has been widely correlated to each compound's octanol- or lipid-water partition coefficient, and thereby its relative tendency to accumulate in lipid regions of the cell membrane at concentrations sufficient to interfere with basic nutrient or ion transport processes [28–32]. Nevertheless, it has been difficult for lipid based theories to account for the cutoff effect and with this deficiency in mind, other researchers have used alkanol inhibition of the lipid-free luciferase enzyme to build a case for anesthetics acting by binding directly to a protein pocket of circumscribed dimension [27, 33–35]. Still, doubt remains as to whether this enzyme adequately models the anesthetic site of general anesthesia in animals [14,36], or for that matter whether anesthetic activity of alkanols is limited to a single mechanism.

The fact that sonication, temperature and combination with a surfactant could be used to manipulate mosquitocidal activity nearly ten-fold around the cutoff supports the notion that the solubility of alkanols in biological membranes and their capacity to perturb membrane lipids at the lipid-protein interface have some bearing on explanation of the cutoff phenomenon. Indeed, there are several recent studies to support this hypothesis. Anesthetic chain lengths were shown to cause perturbation of membrane lipids whereas nonanesthetic alkanols dissolved in membrane lipids without perturbing them [22]. FTIR studies of lipid membrane vesicles in $D_2O$ showed that hydrogen bonding of the alkanol hydroxyl to the phosphate moiety in reversed micelles increases up to decanol, and then declines sharply at tetradecanol [23]. If alkanols bond to the phosphate moiety in biological membranes the way they do in membrane vesicles, then certainly they would affect the conformation and function of proteins normally held in place by hydrogen bonds at the lipid-protein interface.

Alkanols are colorless, inexpensive, biodegradable [37] and essentially non-toxic to humans [38]. That they are already approved for use in food products at concentrations comparable to the doses used here [4] may facilitate their approval as insecticides. Furthermore the more narrow spectrum activity of tridecanol, tetradecanol, and pentadecanol against mosquitoes makes these particularly useful for environmentally sensitive pest management programs.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of mosquito abatement comprising the steps of determining that a water source contains mosquito larvae and administering to the water source an effective amount of a water-insoluble alcohol toxic to mosquito larvae, wherein the alcohol is in a water-miscible form and has a chain length of 13–16 carbon atoms if saturated and 13–18 carbon atoms if unsaturated, whereby the viability of the mosquito larvae is reduced.

2. The method of claim 1 wherein said water-miscible form comprises a surfactant.

3. The method of claim 1 wherein said water-miscible form comprises a surfactant and said surfactant is a detergent.

4. The method of the claim 1 wherein the alcohol is primary, secondary or tertiary, non-aromatic, unsubstituted, saturated or unsaturated, and branched or unbranched.

5. The method of claim 1 wherein the alcohol is nonaromatic, non-cyclic, unsubstituted, unbranched and has 13 to 15 carbon atoms.

6. The method of claim 1 wherein the administering step is nontoxic to tadpoles and minnows.

7. The method of claim 1 wherein the alcohol demonstrates $LD_{50}$ toxicity to the mosquito larvae at less than 30 µg/ml at 24 hr exposure.

8. The method of claim 1 wherein the alcohol demonstrates $LD_{50}$ toxicity to the mosquito larvae at less than 3 µg/ml at 24 hr exposure.

9. The method of claim 4 wherein the alcohol demonstrates $LD_{50}$ toxicity to the mosquito larvae at less than 30 µg/ml at 24 hr exposure.

10. The method of claim 4 wherein the alcohol demonstrates $LD_{50}$ toxicity to the mosquito larvae at less than 3 µg/ml at 24 hr exposure.

11. The method of claim 1 wherein the water-miscible form increases the effective volumetric concentration of the alcohol over diffusion from a surface application by at least one order of magnitude.

12. The method of claim 1 wherein the water-miscible form increases the effective volumetric concentration of the alcohol over diffusion from a surface application by at least three orders of magnitude.

13. The method of claim 1 wherein the alcohol is a primary alkanol with 13 to 15 carbon atoms.

14. The method of claim 1 wherein the alcohol is tridecanol.

15. The method of claim 1 wherein the alcohol is tetradecanol.

16. The method of claim 1 wherein the alcohol is pentadecanol.

17. The method of claim 1 wherein the alcohol is tridecanol and said water-miscible form comprises a surfactant.

18. The method of claim 1 wherein the alcohol is tetradecanol and said water-miscible form comprises a surfactant.

19. The method of claim 1 wherein the alcohol is pentadecanol and said water-miscible form comprises a surfactant.

20. The method of claim 1 wherein the alcohol is selected from cis-11-hexadecen-1-ol, linoleyl alcohol, linolenyl alcohol, cardol 15:3, anacardic acid and cardanol 15:0.

21. The method of claim 1 wherein the alcohol is selected from cis-11-hexadecen-1-ol, linoleyl alcohol, linolenyl alcohol, cardol 15:3, anacardic acid and cardanol 15:0, and said water-miscible form comprises a surfactant.

* * * * *